(12) United States Patent
Shinji et al.

(10) Patent No.: US 10,905,314 B2
(45) Date of Patent: Feb. 2, 2021

(54) ILLUMINATION DEVICE AND ENDOSCOPE

(71) Applicant: OLYMPUS CORPORATION, Hachioji (JP)

(72) Inventors: Sho Shinji, Tokyo (JP); Kazunari Hanano, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 363 days.

(21) Appl. No.: 15/974,897

(22) Filed: May 9, 2018

(65) Prior Publication Data

US 2018/0256014 A1 Sep. 13, 2018

Related U.S. Application Data

(63) Continuation of application No. PCT/JP2015/084009, filed on Dec. 3, 2015.

(51) Int. Cl.
*A61B 1/00* (2006.01)
*A61B 1/06* (2006.01)
(Continued)

(52) U.S. Cl.
CPC ...... *A61B 1/00174* (2013.01); *A61B 1/00096* (2013.01); *A61B 1/00165* (2013.01);
(Continued)

(58) Field of Classification Search
None
See application file for complete search history.

(56) References Cited

U.S. PATENT DOCUMENTS

| | | |
|---|---|---|
| 2008/0242935 A1 | 10/2008 | Inoue |
| 2013/0137923 A1 | 5/2013 | Honda et al. |
| 2014/0347878 A1* | 11/2014 | Honda ............... A61B 1/00177 362/574 |
| 2014/0362599 A1 | 12/2014 | Ohno et al. |
| 2016/0103312 A1 | 4/2016 | Furuta |

FOREIGN PATENT DOCUMENTS

| | | |
|---|---|---|
| EP | 2649923 A1 | 10/2013 |
| EP | 2815691 A1 | 12/2014 |

(Continued)

OTHER PUBLICATIONS

International Search Report (ISR) dated Mar. 1, 2016 issued in International Application No. PCT/JP2015/084009.

(Continued)

*Primary Examiner* — Timothy J Neal
(74) *Attorney, Agent, or Firm* — Holtz, Holtz & Volek PC

(57) ABSTRACT

For the purpose of performing illumination with which vignetting of illumination light caused by a structure is alleviated, thus making the difference between a bright part and a dark part on an object less noticeable, an illumination device according to the present invention is provided with: a light-emitting part that has an emission end from which illumination light is emitted; a diffusion optical member that is disposed around a predetermined axis in the circumferential direction, that is provided with an incident end disposed so as to be opposed to the emission end, that guides the illumination light entering from the incident end while diffusing the illumination light, and that emits the illumination light from a surface thereof; and a reflective layer that is disposed adjacent to a radially inward surface of the diffusion optical member and that reflects the illumination light radially outward, wherein an angle, around the axis, of an emission region for the illumination light in the diffusion optical member is reduced as the distance from the incident end is increased in the axial direction.

13 Claims, 11 Drawing Sheets

(51) Int. Cl.
*A61B 1/07* (2006.01)
*G02B 23/24* (2006.01)
(52) U.S. Cl.
CPC .......... *A61B 1/0607* (2013.01); *A61B 1/0615* (2013.01); *A61B 1/0623* (2013.01); *A61B 1/0676* (2013.01); *A61B 1/07* (2013.01); *G02B 23/2469* (2013.01)

(56) References Cited

FOREIGN PATENT DOCUMENTS

| | | | |
|---|---|---|---|
| EP | 3020321 | A1 | 5/2016 |
| JP | 2008237790 | A | 10/2008 |
| JP | 2014155526 | A | 8/2014 |
| JP | 2014241227 | A | 12/2014 |
| JP | 2015016021 | A | 1/2015 |
| WO | 2012137737 | A1 | 10/2012 |
| WO | 2014073426 | A1 | 5/2014 |
| WO | 2015005159 | A1 | 1/2015 |

OTHER PUBLICATIONS

Written Opinion dated Mar. 1, 2016 issued in International Application No. PCT/JP2015/084009.

* cited by examiner

ILLUMINATION DEVICE AND ENDOSCOPE

CROSS-REFERENCE TO RELATED APPLICATIONS

This application is based on International Patent Application No. PCT/JP2015/084009, the contents of which are incorporated herein by reference.

TECHNICAL FIELD

The present invention relates to an illumination device and an endoscope.

BACKGROUND ART

The angle of view of an endoscope is usually 180 degrees or less, and the field of view in the traveling direction (hereinafter, referred to as a forward field of view) can be easily observed within the range of the angle of view, but a rear field of view with respect to the traveling direction cannot be observed. In particular, in an endoscope for large intestine, there is a possibility of overlooking a lesion or a disease existing behind the large number of folds in the large intestine. In order to observe the back sides of the folds, the distal end of the endoscope is bent rearward for observation; however, it is cumbersome to bend the endoscope for observation for each of a large number of folds.

Thus, desired is an endoscope for the large intestine that has a wide angle of view in which a forward field of view, a side field of view, and a rear field of view can be observed at once (for example, see PTL 1).

In the endoscope of PTL 1, a single imaging optical system captures the forward field of view and the side field of view, thus making it possible to acquire an image having a wide angle of view of 180 degrees or greater. Accordingly, an operator can observe the back sides of the folds without bending the endoscope.

CITATION LIST

Patent Literature

{PTL 1} Japanese Unexamined Patent Application, Publication No. 2015-16021

SUMMARY OF INVENTION

Technical Problem

An object of the present invention is to provide an illumination device and an endoscope capable of performing illumination with which vignetting of illumination light caused by a structure is alleviated, thus making the difference between a bright part and a dark part of an object less noticeable.

Solution to Problem

According to one aspect, the present invention provides an illumination device including: a light-emitting part that has an emission end from which illumination light is emitted; a diffusion optical member that is disposed around a predetermined axis in the circumferential direction, that is provided with an incident end disposed so as to be opposed to the emission end, that guides the illumination light entering from the incident end while diffusing the illumination light, and that emits the illumination light from a surface thereof; and a reflective layer that is disposed adjacent to a radially inward surface of the diffusion optical member and that reflects the illumination light radially outward, wherein an angle, around the axis, of an emission region for the illumination light, in the diffusion optical member is reduced as the distance from the incident end is increased in the axial direction.

In the above-described aspect, the diffusion optical member may be provided with a notch portion having a shape in which a part of circumferential section of a cylinder is removed along the entire length thereof in the axial direction and may also be provided with, at a section thereof close to the notch portion, an inclined surface that has a shape with which a notch angle is increased as the distance from the incident end is increased in the axial direction.

In the above-described aspect, the inclined surface may be provided with a reflecting means that reflects the illumination light that has been guided inside the diffusion optical member, toward the inside of the diffusion optical member.

In the above-described aspect, the inclined surface may be a flat surface.

In the above-described aspect, the angle between the inclined surface and the axis may be equal to or greater than 20 degrees and may be equal to or less than 70 degrees.

In the above-described aspect, the inclined surface may have, at a section thereof close to the incident end, a surface whose angle with respect to the axis is less than the angle between the inclined surface and the axis.

In the above-described aspect, at least a partial section of the emission end may be disposed at a position of the incident end that overlaps with the inclined surface in the circumferential direction.

In the above-described aspect, the notch angle may be equal to or greater than 100 degrees and may be equal to or less than 240 degrees at a position farthest from the incident end of the diffusion optical member in the axial direction.

In the above-described aspect, the diffusion optical member may have approximately a fan shape in transverse section perpendicular to the axis.

The above-described aspect may further include a light-shielding member that applies light shielding such that the angle, around the axis, of the emission region in the diffusion optical member is reduced as the distance from the incident end is increased in the axial direction.

The above-described aspect may further include a light-shielding region that limits an emission region for the illumination light in the diffusion optical member to a partial section around the axis in the circumferential direction, wherein an angle, around the axis, of the light-shielding region is equal to or greater than 100 degrees and is equal to or less than 240 degrees at a position farthest from the incident end of the diffusion optical member in the axial direction.

In the above-described aspect, the diffusion optical member may be provided with a notch portion having a shape in which a part of circumferential section of a cylinder is removed along the entire length thereof in the axial direction; and an angle, around the axis, of a notch angle of the notch portion may be equal to or greater than 100 degrees and may be equal to or less than 240 degrees at a position farthest from the incident end of the diffusion optical member in the axial direction.

In the above-described aspect, the diffusion optical member may have approximately a fan shape in transverse section perpendicular to the axis.

According to still another aspect, the present invention provides an endoscope including: one of the above-described illumination devices; an imaging optical system that is disposed along the axis of the illumination device; and an air-supply or water-supply nozzle that is disposed at the opposite side from the emission region across the axis.

In the above-described aspect, the axis may be a central axis of the imaging optical system.

DESCRIPTION OF EMBODIMENTS

An illumination device 4 and an endoscope 1 according to one embodiment of the present invention will be described below with reference to the drawings.

Figure 1:
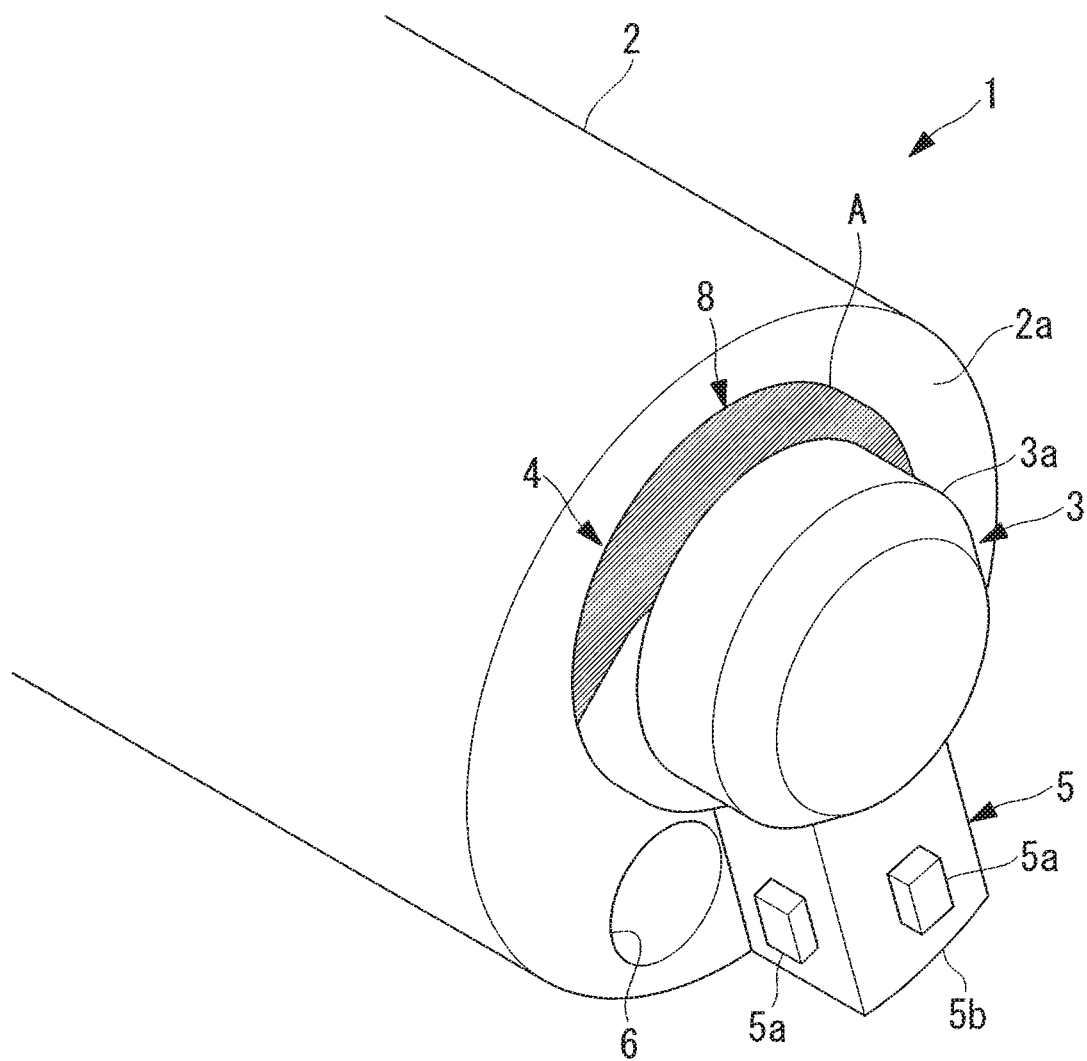
FIG. 1 is a perspective view showing a distal end portion of an endoscope according to one embodiment of the present invention.
Figure 2:
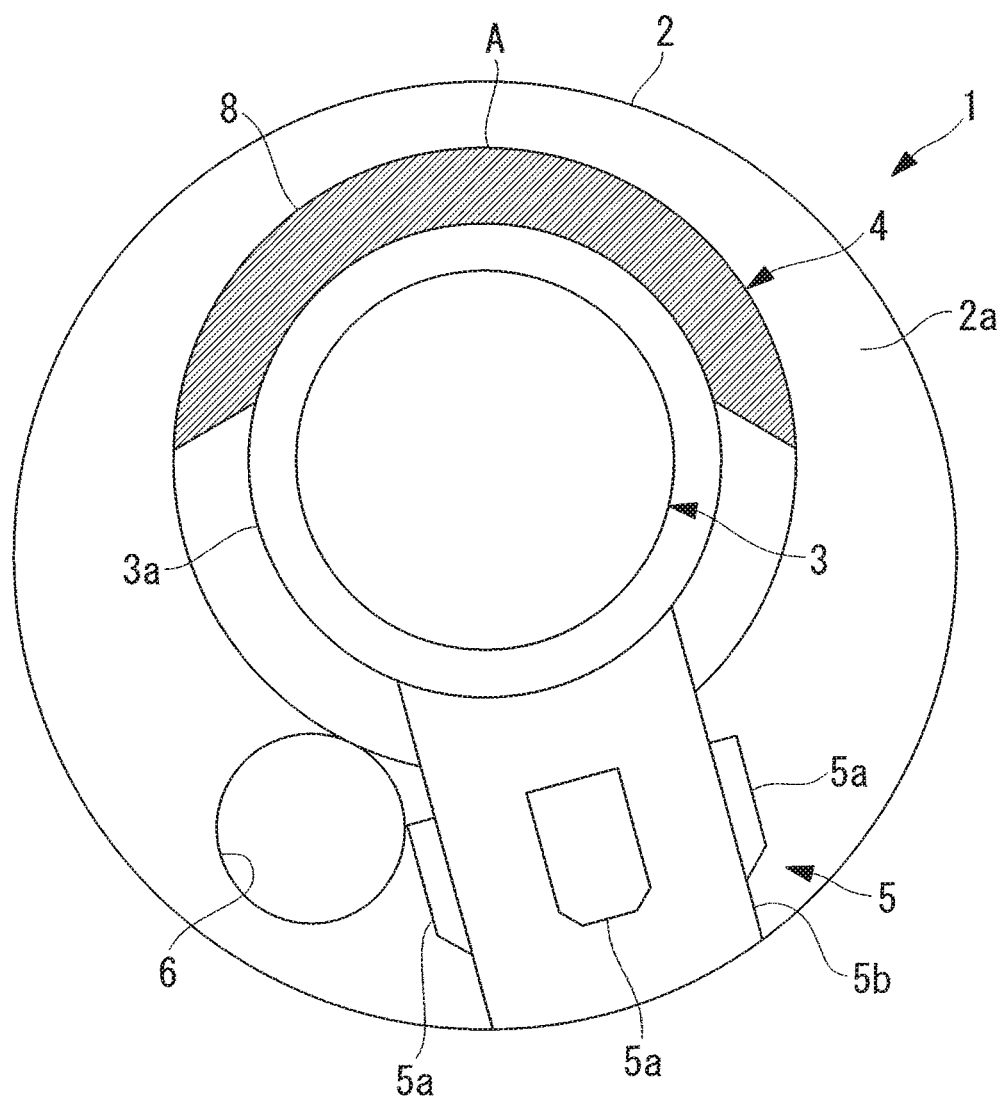
FIG. 2 is a front view showing a distal end portion of an insertion portion of the endoscope shown in FIG. 1.

As shown in FIGS. 1 and 2, the endoscope 1 of this embodiment is provided with, on a distal-end surface 2a of an insertion portion 2, an imaging optical system 3, the illumination device 4 of this embodiment, and a cleaning part (structure) 5 that has air-supply or water-supply nozzles 5a. In the figure, reference sign 6 denotes a forceps opening through which a treatment tool or the like is made to pass.

Figure 3:
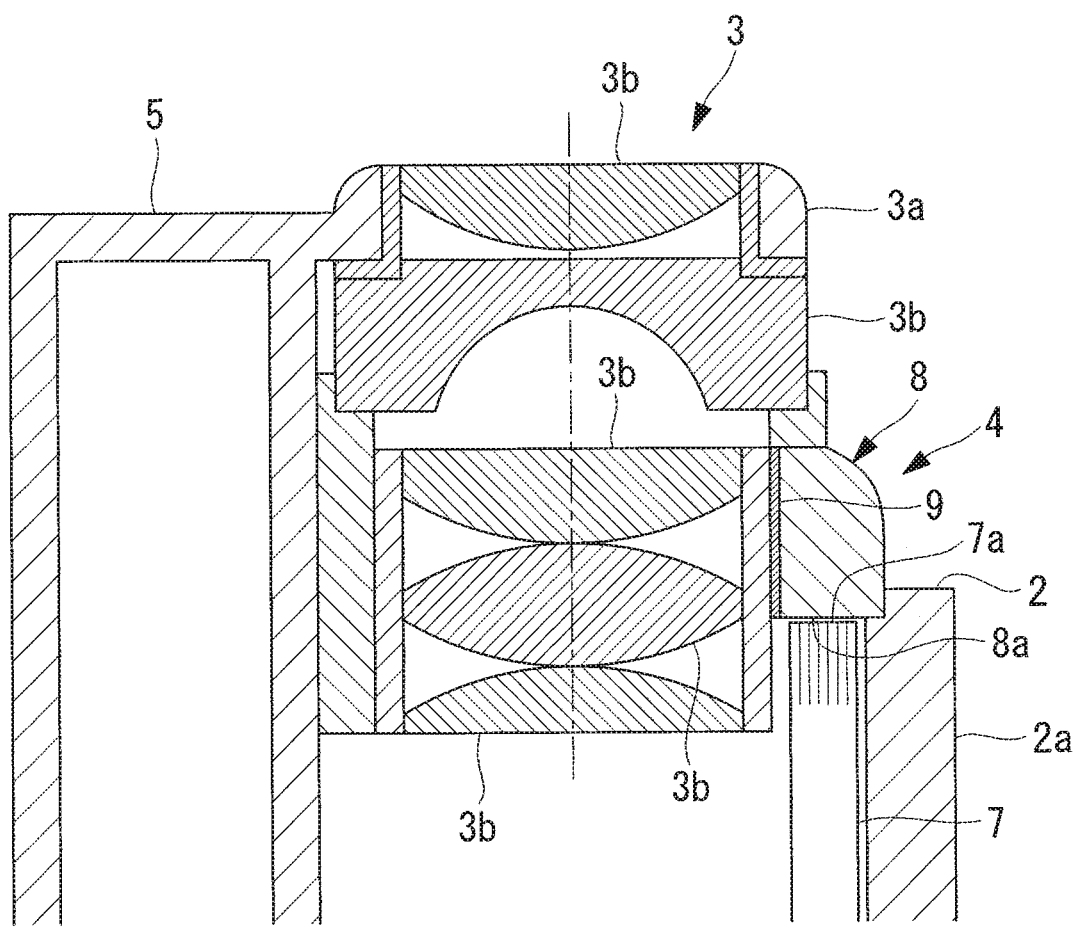
FIG. 3 is a longitudinal-sectional view showing the distal end portion of the insertion portion of the endoscope shown in FIG. 1.

As shown in FIG. 3, the imaging optical system 3 is provided with, at a position eccentric with respect to the longitudinal axis of the insertion portion 2 of the endoscope 1, a cylindrical housing 3a that protrudes from the distal-end surface 2a along an axis parallel to the longitudinal axis and a plurality of lenses 3b that are accommodated in the housing 3a and that are arranged along the longitudinal axis of the housing 3a. The imaging optical system 3 has an angle of view of 180 degrees or greater toward front and lateral sides.

Figure 4:
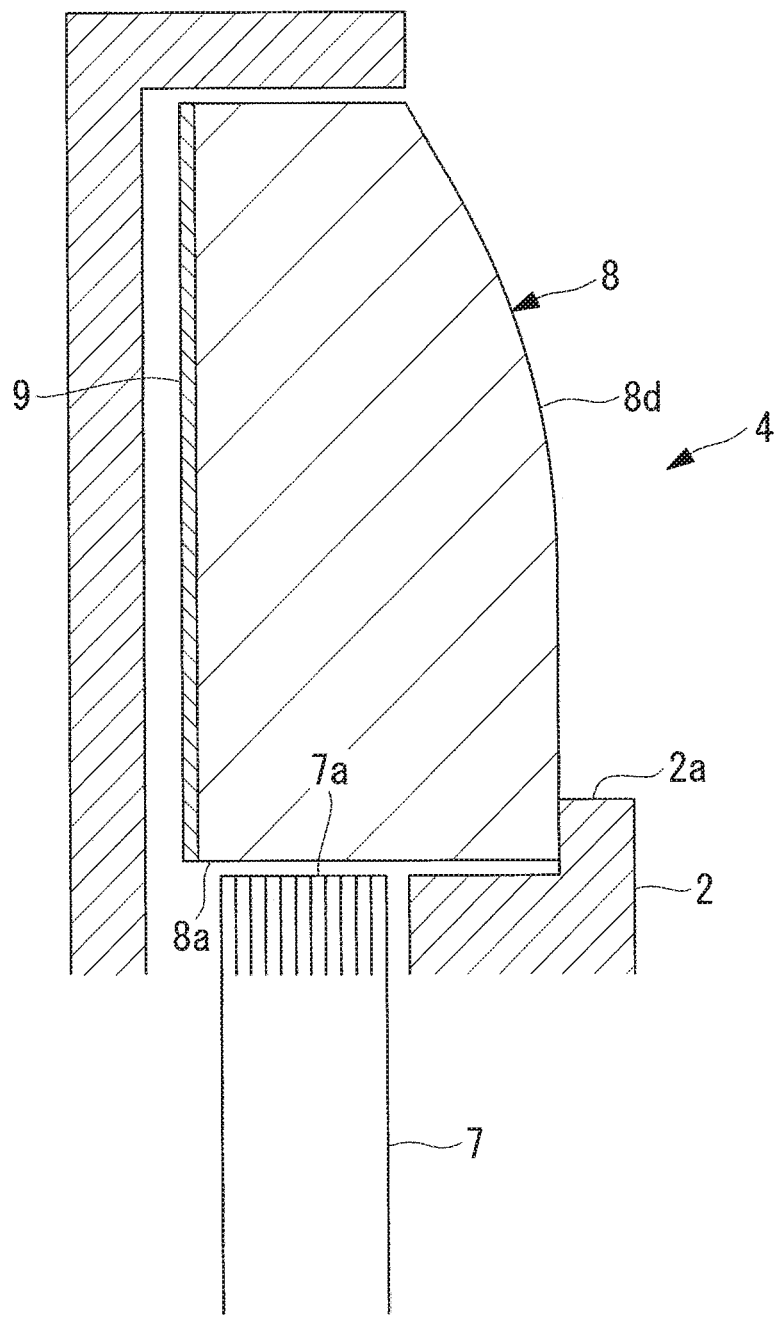
FIG. 4 is a partial longitudinal-sectional view for explaining an illumination device according to the one embodiment of the present invention.

As shown in FIGS. 3 and 4, the illumination device 4 of this embodiment is provided with: fiber bundles (light-emitting parts) 7 that have emission ends 7a from which illumination light guided from a light source (not shown) is emitted; and a diffusion optical member 8 on which the illumination light emitted from the emission ends 7a of the fiber bundles 7 is incident and that guides the received illumination light while diffusing the illumination light. The fiber bundles 7 and the diffusion optical member 8 are disposed around the longitudinal axis of the housing 3a of the imaging optical system 3 in the circumferential direction.

Figure 5A:
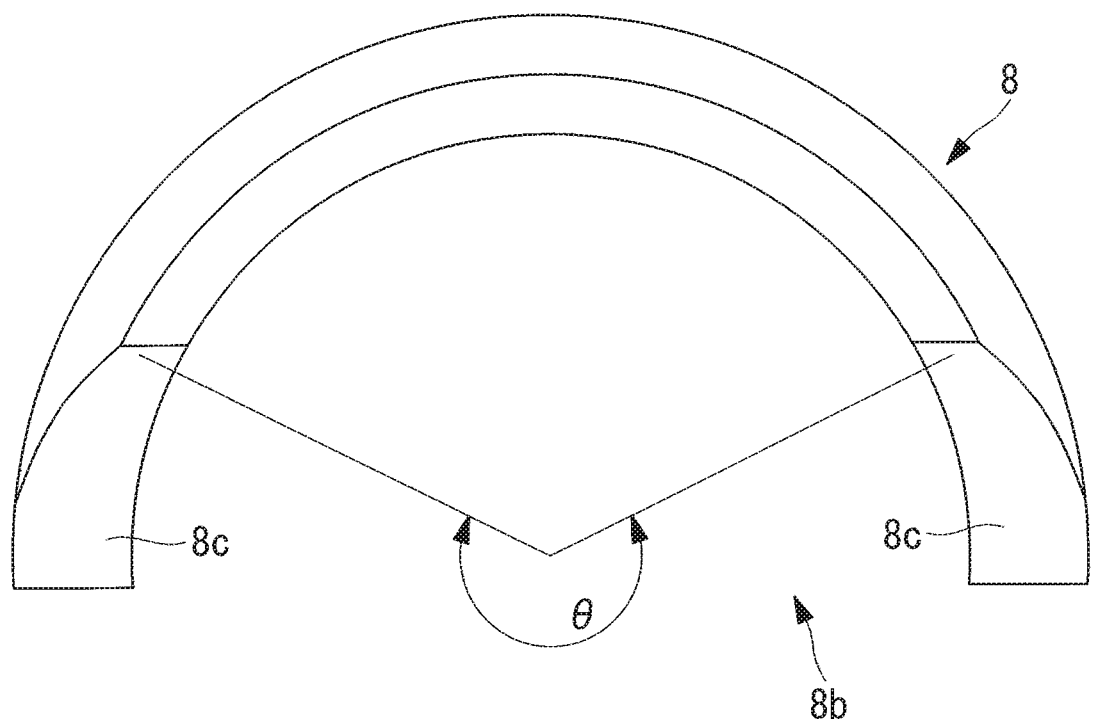
FIG. 5A is a plan view showing a diffusion optical member that is provided in the illumination device shown in FIG. 4.

As shown in FIG. 5A, the diffusion optical member 8 is a member having approximately a C-shape in transverse section (cross section cut in a plane perpendicular to the axis) due to a notch portion 8b that has a shape obtained when a part of circumferential section of an annular (cylindrical) shape is removed along the entire length thereof in the axial direction. The diffusion optical member 8 is formed into the above-described shape after diffusing particles, such as titanium oxide, are mixed with a resin material, such as cycloolefin copolymer.

The diffusion optical member 8 is provided with, on one end surface in the axial direction, an incident end 8a that is disposed so as to be opposed to the emission ends 7a of the fiber bundles 7 and on which illumination light emitted from the emission ends 7a is incident.

The diffusion optical member 8 is provided with, on a radially inner surface thereof, a reflective layer 9 having a high reflectance. The reflective layer 9 is formed of a reflective sheet, a reflective pipe, or a reflective coating. Accordingly, illumination light that is diffused inside the diffusion optical member 8 and that is to be emitted toward the radially inner surface is reflected by the reflective layer 9 and is made to return radially outward, inside the diffusion optical member 8.

Figure 5B:
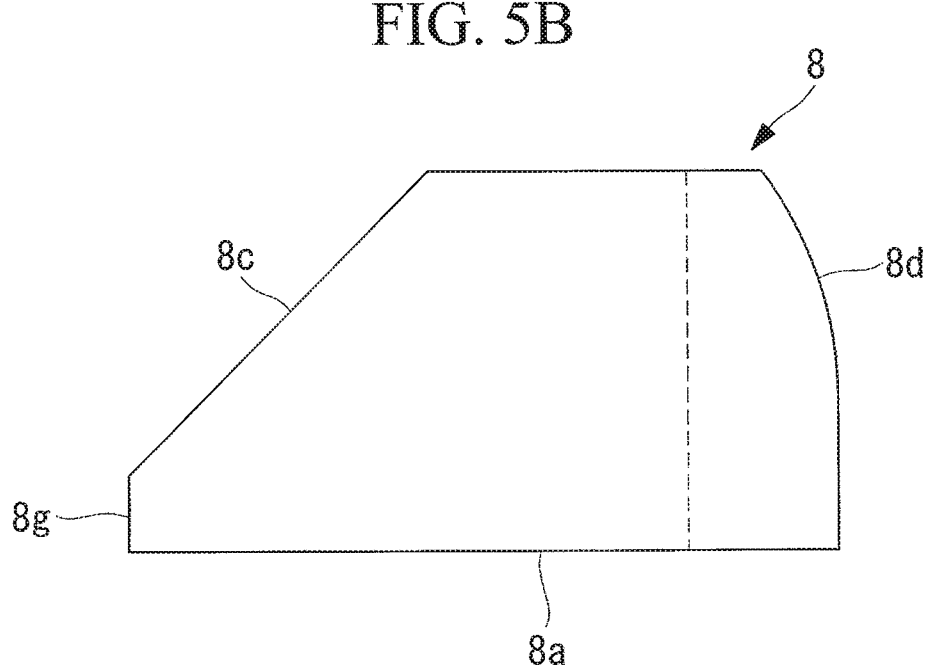
FIG. 5B is a side view showing the diffusion optical member shown in FIG. 5A.

The diffusion optical member 8 is provided with, at both ends of the notch portion 8b thereof, inclined surfaces 8c that are formed of flat surfaces. As shown in FIG. 5B, the inclined surfaces 8c are inclined such that the length of the diffusion optical member 8 in the circumferential direction is reduced from the incident end 8a along the axial direction. In other words, the inclined surfaces 8c are inclined such that the angle of the notch angle of the notch portion 8b, which is formed between the inclined surfaces 8c, is gradually increased from the incident end 8a along the axial direction.

In this embodiment, the angle θ of the notch angle of the notch portion 8b is set to approximately 240 degrees at the position farthest from the incident end 8a in the axial direction, as shown in FIG. 5A. The angle of each of the inclined surfaces 8c with respect to the axis of the diffusion optical member 8 is set to approximately 45 degrees.

An outer peripheral surface 8d that is located radially outward of the diffusion optical member 8 is formed of a smooth curved surface without roughness. Then, as shown in FIGS. 1 and 2, the diffusion optical member 8 is fixed to the distal end of the insertion portion 2 of the endoscope 1 such that only the outer peripheral surface 8d, which is located radially outward thereof, is exposed. Accordingly, the exposed outer peripheral surface 8d constitutes an emission region (shaded area) A where illumination light is emitted.

Figure 6:
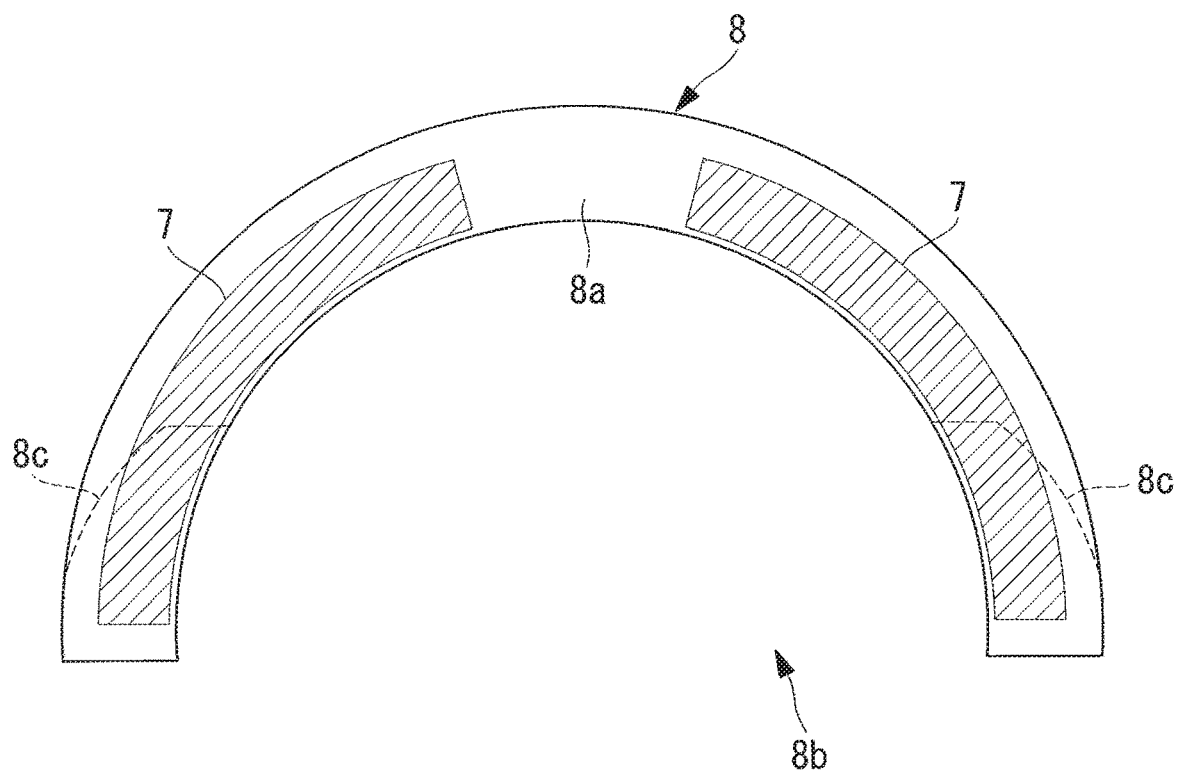
FIG. 6 is a view showing an example arrangement of fiber bundles with respect to an incident end of the diffusion optical member shown in FIG. 5A.

In this embodiment, as shown in FIG. 6, the fiber bundles 7 are disposed, at two places in an arc-like manner, so as to be opposed to the incident end 8a of the diffusion optical member 8. Partial sections of the fiber bundles 7 at the respective places are disposed at positions overlapping with the inclined surfaces 8c in the circumferential direction. Accordingly, illumination light emitted from the partial sections of the emission ends 7a of the fiber bundles 7 travels inside the diffusion optical member 8 while being diffused in the axial direction and is deflected by the inner surfaces of the inclined surfaces 8c, thus being directed in the circumferential direction.

The cleaning part 5 is provided with the plurality of water-supply or air-supply nozzles 5a disposed on a distal-end surface and circumferential side surfaces of a cover 5b that extends in one radially outward direction of the housing 3a of the imaging optical system 3, that protrudes from the distal-end surface 2a of the insertion portion 2, and that is approximately a rectangular parallelepiped. The cleaning part 5 is disposed at the opposite side from the emission region A across the axis of the imaging optical system 3.

The operation of the thus-configured illumination device 4 and endoscope 1 of this embodiment will be described below.

According to the illumination device 4 of this embodiment, when illumination light guided from the light source by the fiber bundles 7 is emitted from the emission ends 7a of the fiber bundles 7, the illumination light is incident on the incident end 8a of the diffusion optical member 8, which is disposed so as to be opposed to the emission ends 7a.

The illumination light that has entered the diffusion optical member 8 is guided while being diffused inside the diffusion optical member 8, and part of the illumination light that is to be emitted radially inward is made to return radially outward by the reflective layer 9. The illumination light that has reached the inclined surfaces 8c, which constitute the notch portion 8b, is deflected at the inner sides of the inclined surfaces 8c and is directed in the circumferential direction.

Then, the illumination light that has been repeatedly diffused inside the diffusion optical member 8 is emitted to the outside from the outer peripheral surface 8d, which constitutes the emission region A and which is located radially outward, thus making it possible to illuminate a subject disposed outside.

In this case, according to the illumination device 4 of this embodiment, because the emission region A is disposed at the opposite side from the cleaning part 5 across the central axis of the imaging optical system 3, it is possible to alleviate vignetting of illumination light emitted from the emission region A, caused by the cover 5b etc. constituting the cleaning part 5.

Due to the inclined surfaces 8c of the diffusion optical member 8, the angular range of the emission region A is the largest in the vicinity of the distal-end surface 2a of the insertion portion 2 and is reduced as the distance from the distal-end surface 2a is increased toward the front side; thus, a section of the emission region A that is located radially inward and frontward and that is close to the edges of the cover 5b of the cleaning part 5 is kept away from the cover 5b, thereby preventing vignetting of high-intensity illumination light just emitted from the emission region A caused by the cover 5b and making it possible to make the difference in illumination between a bright part and a dark part on a subject less noticeable. On the other hand, a section of the emission region A that is located radially outward and rearward and that is relatively distant from the edges of the cover 5b of the cleaning part 5 is broadened as much as possible, thereby making it possible to achieve an expansion of the illumination range.

Because the incident end 8a, which is opposed to the fiber bundles 7, is largely secured due to the inclined surfaces 8c of the diffusion optical member 8, there is an advantage in that it is possible to secure a large amount of illumination light that enters the diffusion optical member 8.

Because illumination light is deflected in the circumferential direction by the inclined surfaces 8c of the diffusion optical member 8, there is an advantage in that the incident illumination light is effectively used without being wasted, thus making it possible to improve the uniformity of illumination light and to improve the illumination efficiency.

In this embodiment, although the angle θ of the notch angle of the notch portion 8b is set to approximately 240 degrees at a position farthest from the incident end 8a in the axial direction, this angle may be set to any value from 100 degrees to 240 degrees. The angle is set to 100 degrees or greater, thereby making it possible to broaden a dark region on a subject and to make the difference between a dark part and a bright part due to vignetting caused by the cover 5b of the cleaning part 5 less noticeable. The angle is set to 240 degrees or less, thereby making it possible to prevent the dark region on the subject from being excessively broadened and to secure a sufficient amount of illumination light for the dark part.

In this embodiment, although the angle of each of the inclined surfaces 8c with respect to the axis of the diffusion optical member 8 is set to approximately 45 degrees, this angle may be set to any value from 20 degrees to 70 degrees.

If this angle is less than 20 degrees, there is a problem in that the effect of the inclined surfaces 8c, which deflect illumination light in the circumferential direction, is reduced, and, if this angle is greater than 70 degrees, there is a problem in that illumination light entering from the incident end 8a is made to return toward the incident end 8a, thus reducing the illumination efficiency.

Figure 7A:
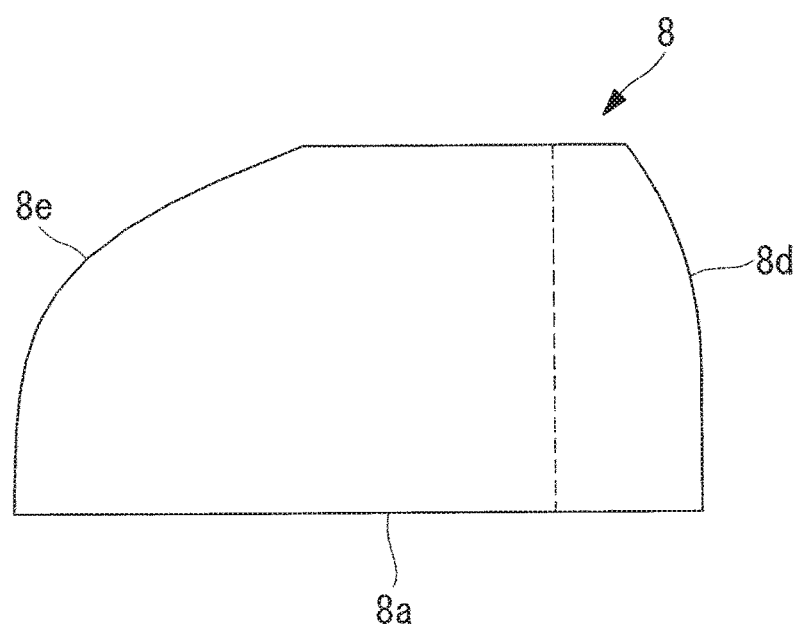
FIG. 7A is a side view showing a modification of the diffusion optical member shown in FIG. 5B.
Figure 7B:
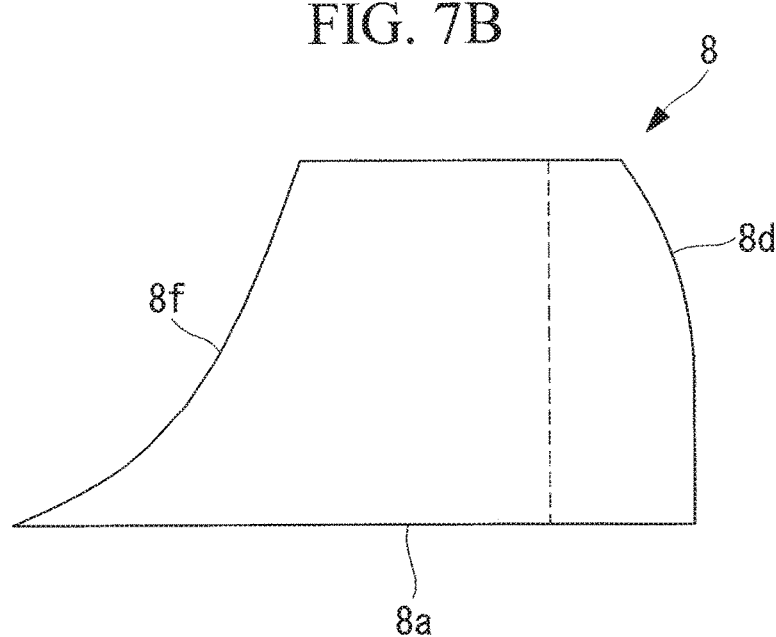
FIG. 7B is a side view showing another modification of the diffusion optical member shown in FIG. 5B.

In this embodiment, although the inclined surfaces 8c are formed of flat surfaces, instead of this, as shown in FIGS. 7A and 7B, the inclined surfaces 8c may be formed of convex curved surfaces 8e or concave curved surfaces 8f. As shown in FIG. 5B, for the purpose of preventing chipping, surfaces (chamfered surfaces) 8g whose angles are less than the inclined surfaces 8c may also be provided at boundary sections between the incident end 8a and the inclined surfaces 8c.

The inclined surfaces 8c may also be provided with high-reflectance reflective layers (reflecting means, not shown). By doing so, the amount of illumination light deflected by the inclined surfaces 8c is increased, thus making it possible to improve the illumination efficiency.

Figure 8:
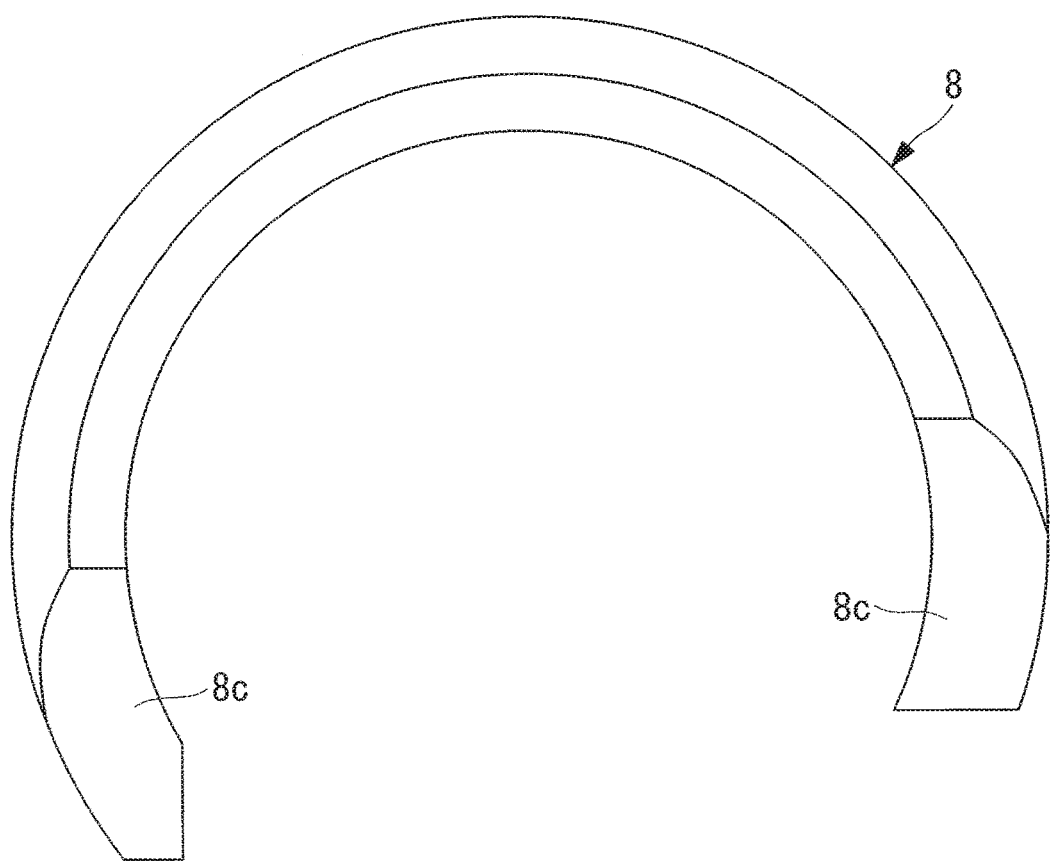
FIG. 8 is a plan view showing a modification of the diffusion optical member shown in FIG. 5A.

As shown in FIG. 2, because the cleaning part 5 is disposed at a position asymmetric with respect to the imaging optical system 3, the diffusion optical member 8 may be formed into an asymmetric shape in accordance with the disposition of the cleaning part 5, as shown in FIG. 8.

Figure 9A:
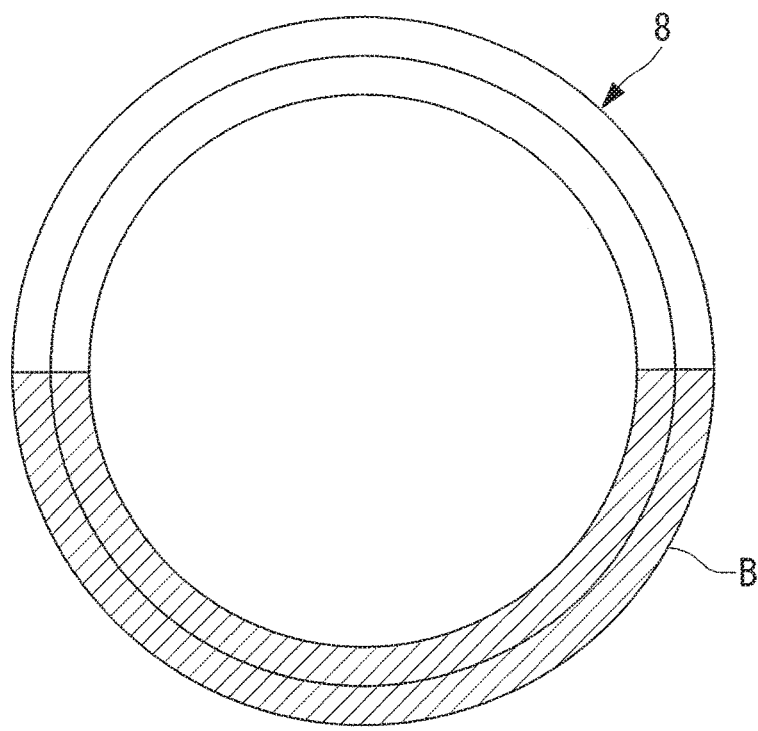
FIG. 9A is a plan view for explaining a modification of the diffusion optical member shown in FIG. 5A and a light-shielding region.
Figure 9B:
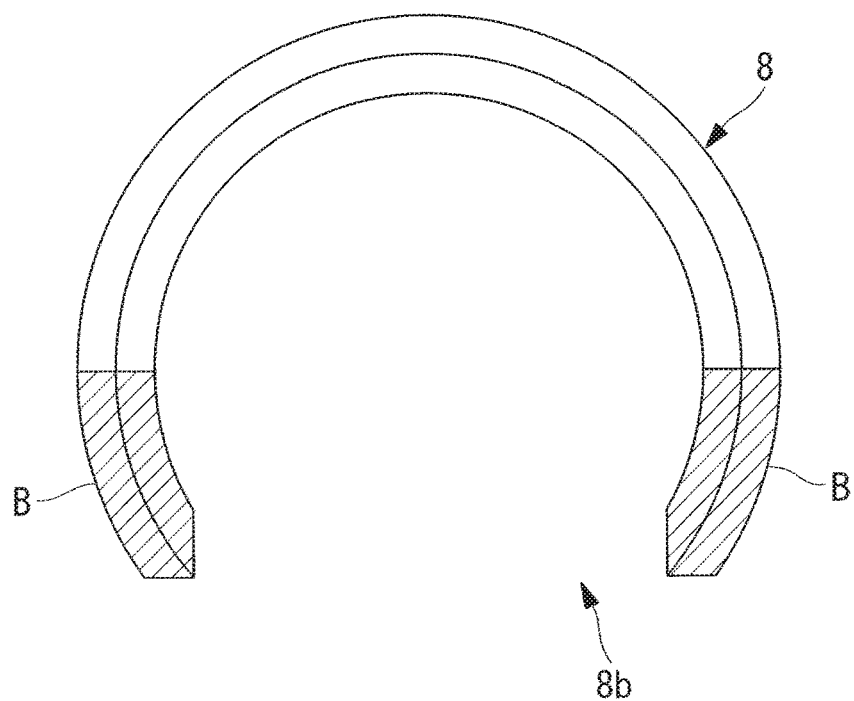
FIG. 9B is a plan view for explaining a modification of the diffusion optical member and the light-shielding region shown in FIG. 9A.

In this embodiment, although the notch portion 8b, which has the inclined surfaces 8c, constitutes a light-shielding region where illumination light is not emitted from the notch portion 8b, instead of this, as shown in FIG. 9A, it is also possible to configure a light-shielding region B (shaded area) by covering a part of circumferential section of an annular diffusion optical member 8 with a light-shielding member (not shown), without providing the notch portion 8b. Alternately, as shown in FIG. 9B, it is also possible to configure light-shielding regions B by covering sections in the vicinity of the notch portion 8b with light-shielding members, without providing the inclined surfaces 8c.

Figure 9C:
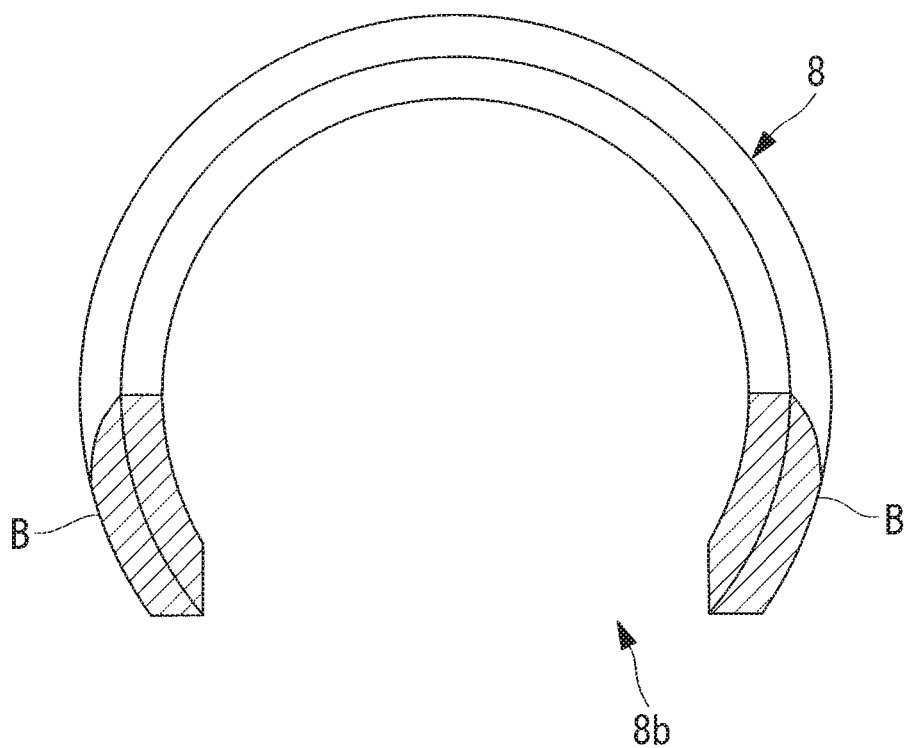
FIG. 9C is a plan view for explaining another modification of the diffusion optical member and the light-shielding region shown in FIG. 9A.
Figure 10A:
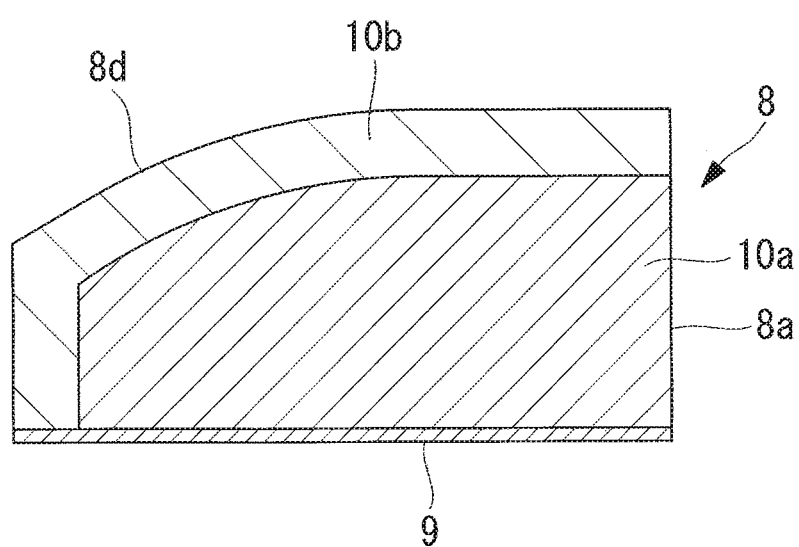
FIG. 10A is a longitudinal-sectional view showing a modification of the diffusion optical member shown in FIG. 5A.
Figure 10B:
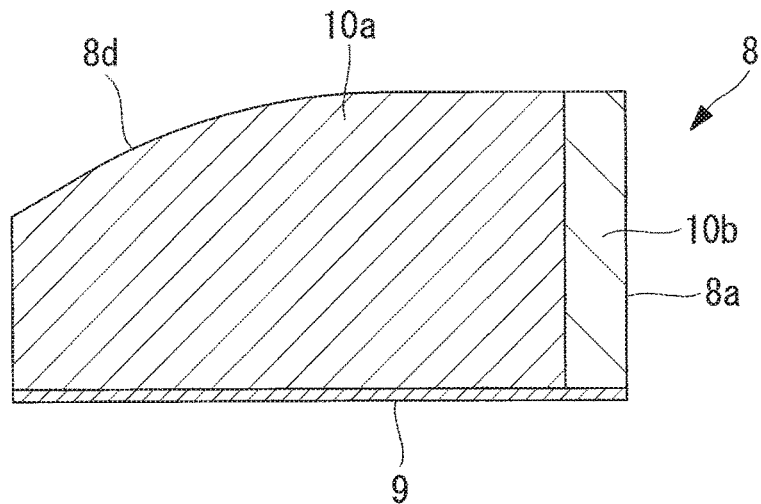
FIG. 10B is a longitudinal-sectional view showing another modification of the diffusion optical member shown in FIG. 5A.
Figure 10C:
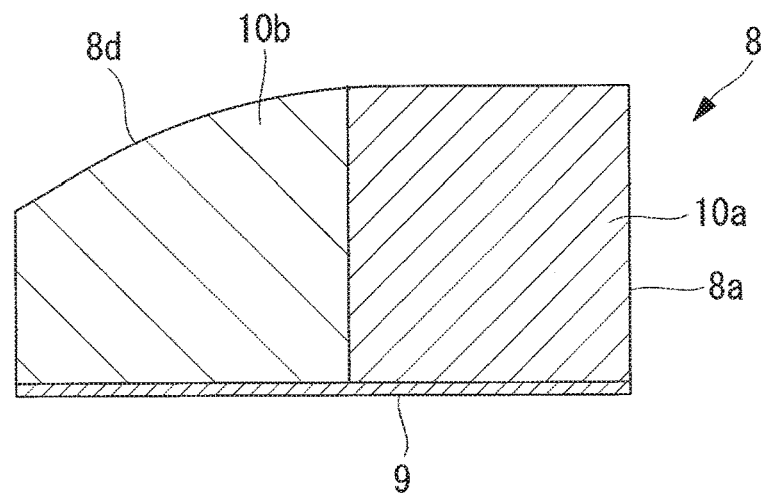
FIG. 10C is a longitudinal-sectional view showing still another modification of the diffusion optical member shown in FIG. 5A.
Figure 10D:
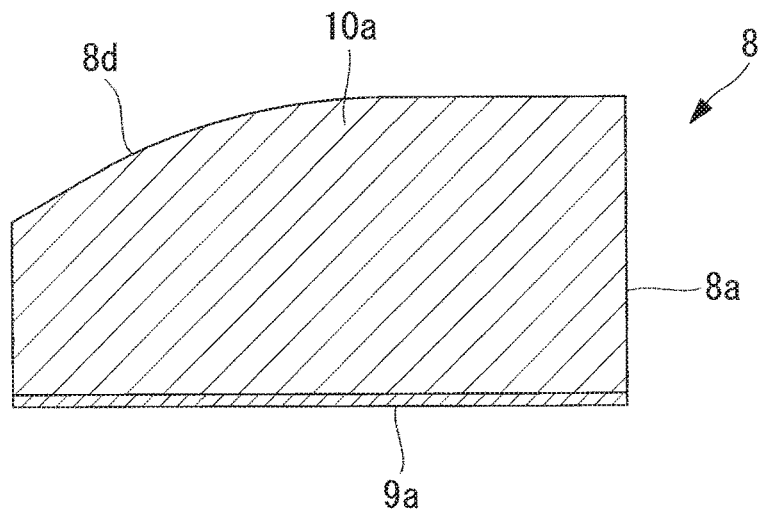
FIG. 10D is a longitudinal-sectional view showing still another modification of the diffusion optical member shown in FIG. 5A.

As shown in FIG. 9C, the emission region A, which is inclined so as to be narrowed from the incident end 8a along the axial direction, can also be configured through covering with light-shielding members, without providing the inclined surfaces 8c.

In this embodiment, although a diffusion optical member obtained by molding a single material in which diffusing particles are mixed with a resin material is shown as the diffusion optical member 8, as shown in FIGS. 10A to 10D, it is also possible to adopt a diffusion optical member having a two-layer structure that is provided with a light guide layer 10a and a diffusion layer 10b or it is also possible to adopt a member having a diffusion effect as the reflective layer 9a, which is disposed radially inward, and to configure the other section by using the light guide layer 10a.

Figure 11A:
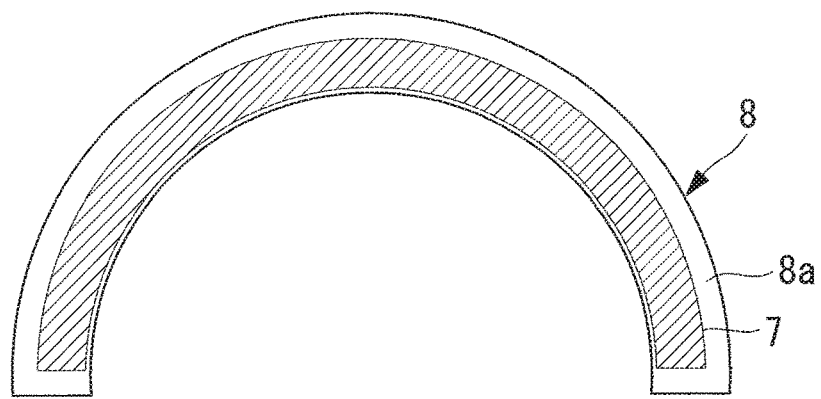
FIG. 11A is a view showing a modification of the arrangement of the fiber bundles with respect to the incident end of the diffusion optical member shown in FIG. 6.
Figure 11B:
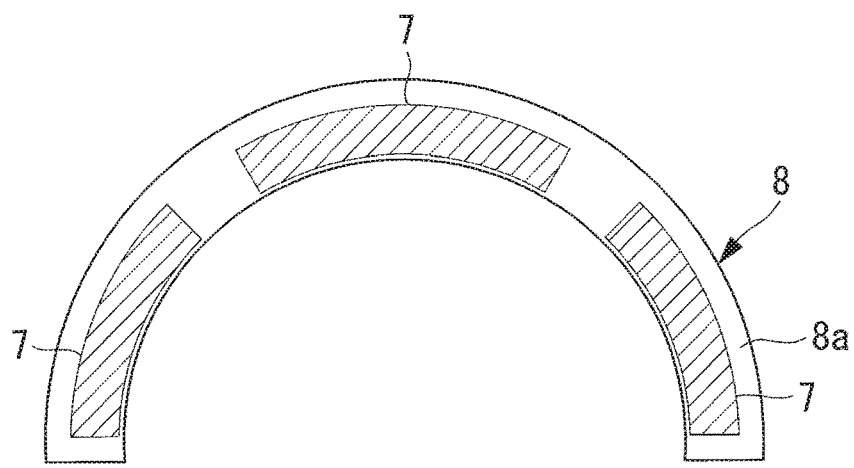
FIG. 11B is a view showing another modification of the arrangement of the fiber bundles with respect to the incident end of the diffusion optical member shown in FIG. 6.
Figure 11C:
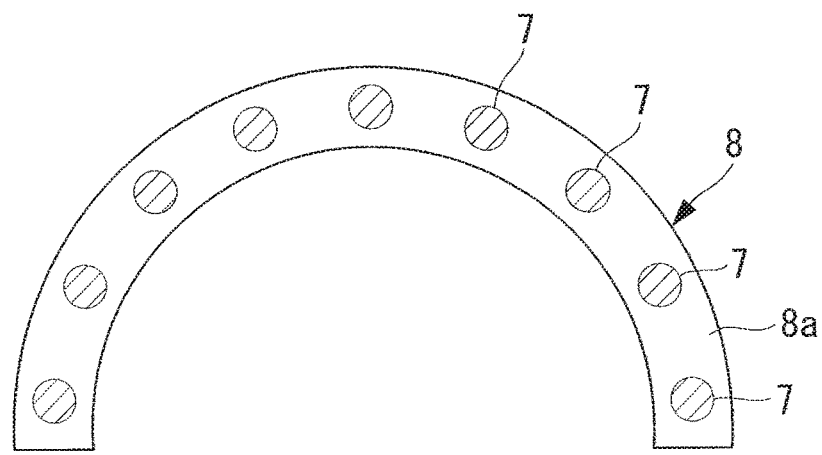
FIG. 11C is a view showing still another modification of the arrangement of the fiber bundles with respect to the incident end of the diffusion optical member shown in FIG. 6.

In this embodiment, although the light-emitting parts are disposed, by means of the emission ends 7a of the fiber bundles 7, at two places in an arc-like manner, it is also possible to dispose a fiber bundle 7 over almost the entire length of the arc-shaped incident end 8a, as shown in FIG. 11A, or to separately dispose fiber bundles 7 at three places or more, as shown in FIG. 11B. Instead of the arc-like arrangement, it is also possible to array fiber bundles 7 that have circular-shaped emission ends 7a, at intervals in the circumferential direction of the incident end 8a, as shown in FIG. 11C. Instead of the fiber bundles 7, it is also possible to dispose light sources (not shown), such as LEDs.

As a result, the following aspect is derived from the above-described embodiment.

According to one aspect, the present invention provides an illumination device including: a light-emitting part that has an emission end from which illumination light is emitted; a diffusion optical member that is disposed around a predetermined axis in the circumferential direction, that is provided with an incident end disposed so as to be opposed to the emission end, that guides the illumination light entering from the incident end while diffusing the illumination light, and that emits the illumination light from a surface thereof; and a reflective layer that is disposed adjacent to a radially inward surface of the diffusion optical member and that reflects the illumination light radially outward, wherein an angle, around the axis, of an emission region for the illumination light, in the diffusion optical member is reduced as the distance from the incident end is increased in the axial direction.

According to this aspect, illumination light emitted from the emission end of the light-emitting part enters the diffusion optical member from the incident end of the diffusion optical member, which is disposed so as to be opposed to the emission end, is guided while being diffused, and is emitted from the surface to the outside. The illumination light to be emitted to the outside from the surface located radially inward of the diffusion optical member is made to return to the inside of the diffusion optical member by the reflective layer, which is disposed adjacent to this surface, and is effectively used as illumination light emitted from another surface. Then, because the angular range of the emission region for the illumination light in the diffusion optical member is the largest on the incident end and is reduced as the distance from the incident end is increased in the axial direction, if a structure is located at the opposite side from the emission region across the axis (i.e., at a region from which light is not emitted, when viewed from the above-described axis), the amount of illumination light to be radiated onto the edges of the structure is reduced, thus making it possible to alleviate vignetting of illumination light caused by the structure. As a result, it is possible to perform illumination that makes the difference between a bright part and a dark part of an object less noticeable.

In the above-described aspect, the diffusion optical member may be provided with a notch portion having a shape in which a part of circumferential section of a cylinder is removed along the entire length thereof in the axial direction and may also be provided with, at a section thereof close to the notch portion, an inclined surface that has a shape with which a notch angle is increased as the distance from the incident end is increased in the axial direction.

By doing so, part of the illumination light entering the diffusion optical member from the incident end in the axial direction can be deflected in the circumferential direction by the inclined surface, thus making it possible to improve the uniformity of illumination light emitted from the emission region.

In the above-described aspect, the inclined surface may be provided with a reflecting means that reflects the illumination light that has been guided inside the diffusion optical member, toward the inside of the diffusion optical member.

By doing so, illumination light entering the diffusion optical member from the incident end in the axial direction can be more effectively deflected in the circumferential direction by the reflecting means, which is disposed on the inclined surface, thus making it possible to achieve effective use of illumination light and to improve the illumination efficiency.

In the above-described aspect, the inclined surface may be a flat surface.

By doing so, it is possible to improve the ease of processing of the diffusion optical member.

In the above-described aspect, the angle between the inclined surface and the axis may be equal to or greater than 20 degrees and may be equal to or less than 70 degrees.

By doing so, it is possible to achieve an improvement of the uniformity of illumination light and an improvement of the illumination efficiency. When the angle between the inclined surface and the axis is less than 20 degrees, the amount of illumination light deflected in the circumferential direction by the inclined surface is small, thus making it impossible to obtain a sufficient effect of the inclined surface. On the other hand, when the angle therebetween is greater than 70 degrees, the amount of illumination light returning toward the incident end is increased, thus reducing the illumination efficiency.

In the above-described aspect, the inclined surface may have, at a section thereof close to the incident end, a surface whose angle with respect to the axis is less than the angle between the inclined surface and the axis.

By doing so, the edge between the inclined surface and the incident end is eliminated, thereby making it possible to prevent damage due to chipping.

In the above-described aspect, at least a partial section of the emission end may be disposed at a position of the incident end that overlaps with the inclined surface in the circumferential direction.

By doing so, illumination light entering from a section of the incident end located at a position overlapping with the inclined surface in the circumferential direction is deflected in the circumferential direction by the inclined surface and is effectively used, thereby making it possible to achieve an improvement of the uniformity of illumination and an improvement of the illumination efficiency.

In the above-described aspect, the notch angle may be equal to or greater than 100 degrees and may be equal to or less than 240 degrees at a position farthest from the incident end of the diffusion optical member in the axial direction.

By doing so, when the notch angle at a position farthest from the incident end in the axial direction is set to 100 degrees or greater, it is possible to broaden a dark region where the amount of illumination light is low, to alleviate vignetting of illumination light, and to make the difference between a bright part and a dark part due to vignetting less noticeable. On the other hand, when the notch angle is set equal to or less than 240 degrees, it is possible to prevent a dark region from being excessively broadened and to secure a sufficient amount of illumination light for a dark part.

In the above-described aspect, the diffusion optical member may have approximately a fan shape in transverse section perpendicular to the axis.

By doing so, the diffusion optical member is formed into a simple shape obtained merely by removing a section of a cylinder, thereby making it possible to improve the ease of manufacturing of the diffusion optical member.

The above-described aspect may further include a light-shielding member that applies light shielding such that the angle, around the axis, of the emission region in the diffusion optical member is reduced as the distance from the incident end is increased in the axial direction.

By doing so, the diffusion optical member can be formed into a simple shape that does not have a notch portion or an inclined surface.

The above-described aspect may further include a light-shielding region that limits an emission region for the illumination light in the diffusion optical member to a partial section around the axis in the circumferential direction, wherein an angle, around the axis, of the light-shielding region is equal to or greater than 100 degrees and is equal to or less than 240 degrees at a position farthest from the incident end of the diffusion optical member in the axial direction.

According to this aspect, the diffusion optical member can be formed into a simple shape that does not have a notch portion or an inclined surface. When the angle of the light-shielding region about the angle at a position farthest from the incident end in the axial direction is set to 100 degrees or greater, it is possible to broaden a dark region where the amount of illumination light is low, to alleviate vignetting of illumination light, and to make the difference between a bright part and a dark part due to vignetting less noticeable. On the other hand, when the angle of the light-shielding region about the angle is set equal to or less than 240 degrees, it is possible to prevent a dark region from being excessively broadened and to secure a sufficient amount of illumination light for a dark part.

In the above-described aspect, the diffusion optical member may be provided with a notch portion having a shape in which a part of circumferential section of a cylinder is removed along the entire length thereof in the axial direction; and an angle, around the axis, of a notch angle of the notch portion may be equal to or greater than 100 degrees and may be equal to or less than 240 degrees at a position farthest from the incident end of the diffusion optical member in the axial direction.

By doing so, the light-shielding region can be formed by the notch portion.

In the above-described aspect, the diffusion optical member may have approximately a fan shape in transverse section perpendicular to the axis.

According to still another aspect, the present invention provides an endoscope including: one of the above-described illumination devices; an imaging optical system that is disposed along the axis of the illumination device; and an air-supply or water-supply nozzle that is disposed at the opposite side from the emission region across the axis.

In the above-described aspect, the axis may be a central axis of the imaging optical system.

REFERENCE SIGNS LIST 1 endoscope
3 imaging optical system
4 illumination device
5a nozzle
7 fiber bundle (light-emitting part)
7a emission end
8 diffusion optical member
8a incident end
8b notch portion
8c inclined surface
9 reflective layer
A emission region
B light-shielding region

The invention claimed is:
1. An illumination device comprising:
a light-emitting part that has an emission end from which illumination light is emitted;
a diffusion optical member that is disposed around a predetermined axis in a circumferential direction, that is provided with an incident end disposed so as to be opposed to the emission end, that guides the illumination light entering from the incident end while diffusing the illumination light, and that emits the illumination light from a surface thereof; and
a reflective layer that is disposed adjacent to a radially inward surface of the diffusion optical member and that reflects the illumination light radially outward,
wherein the diffusion optical member is provided with a notch portion having a shape in which a part of a circumferential section of a cylinder is removed along an entire length thereof in a direction along the predetermined axis and is also provided with, at a section thereof close to the notch portion, an inclined surface having a shape with which a notch angle is increased as a distance from the incident end is increased in the direction along the predetermined axis.

2. The illumination device according to claim 1, wherein the inclined surface is provided with a reflecting means that reflects the illumination light that has been guided inside the diffusion optical member toward the inside of the diffusion optical member.

3. The illumination device according to claim 1, wherein the inclined surface is a flat surface.

4. The illumination device according to claim 3, wherein an angle between the inclined surface and the predetermined axis is equal to or greater than 20 degrees and is equal to or less than 70 degrees.

5. The illumination device according to claim 1, wherein the inclined surface has, at a section thereof close to the incident end, a surface whose angle with respect to the predetermined axis is less than the angle between the inclined surface and the axis.

6. The illumination device according to claim 1, wherein at least a partial section of the emission end is disposed at a position of the incident end that overlaps with the inclined surface in the circumferential direction.

7. The illumination device according to claim 1, wherein the notch angle is equal to or greater than 100 degrees and is equal to or less than 240 degrees at a position farthest from the incident end of the diffusion optical member in the direction along the predetermined axis.

8. The illumination device according to claim 1, wherein the diffusion optical member has a substantially fan shape in transverse section perpendicular to the predetermined axis.

9. The illumination device according to claim 1, further comprising:
a light-shielding region that limits an emission region for the illumination light in the diffusion optical member to a partial section around the predetermined axis in the circumferential direction,
wherein an angle of the light-shielding region around the predetermined axis is equal to or greater than 100 degrees and is equal to or less than 240 degrees at a position farthest from the incident end of the diffusion optical member in the direction along the predetermined axis.

10. The illumination device according to claim 9, wherein the light-shielding region comprises the notch portion.

11. The illumination device according to claim 10, wherein the diffusion optical member has a substantially fan shape in transverse section perpendicular to the predetermined axis.

12. An endoscope comprising:
the illumination device according to claim 1;
an imaging optical system that is disposed along an axis parallel to the predetermined axis; and
an air-supply or water-supply nozzle that is disposed at an opposite side from the emission region across the axis.

13. The endoscope according to claim 12, wherein the axis is a central axis of the imaging optical system.

* * * * *